United States Patent [19]

Huber

[11] Patent Number: 5,536,453
[45] Date of Patent: Jul. 16, 1996

[54] LIGHT SCREENING AGENT

[75] Inventor: Ulrich Huber, Zurich, Switzerland

[73] Assignee: Givaudan-Roure Corporation,, Clifton, N.J.

[21] Appl. No.: 533,335

[22] Filed: Sep. 25, 1995

Related U.S. Application Data

[62] Division of Ser. No. 361,869, Dec. 22, 1994, Pat. No. 5,481,001, which is a continuation of Ser. No. 949,853, Nov. 19, 1992, abandoned.

[30] Foreign Application Priority Data

Mar. 28, 1991 [CH] Switzerland ................ 948/91
Feb. 20, 1992 [CH] Switzerland ................ 512/92

[51] Int. Cl.⁶ .................................. F21V 9/04
[52] U.S. Cl. ............................ 252/589; 252/588
[58] Field of Search ....................... 252/589, 588

[56] References Cited

FOREIGN PATENT DOCUMENTS 0199323  10/1986  European Pat. Off. ........... 548/243
0349418   1/1990  European Pat. Off. ........... 548/243

OTHER PUBLICATIONS

A. Maquestiau et al., J. Heterocycl. Chem. 12(1), 1975, 27.
CA 94(5): 29684c Mass spectral ... –5–ones. Keats et al., p. 481, 1981.
CA 108(13): 111758w Primary ethynamines ... interest. Wentrup et al., p. 563, 1988.
CA 114(22): 220058n Synthesis ... derivatives. El–Essawi et al., p. 189, 1991.

*Primary Examiner*—Joseph K. McKane
*Attorney, Agent, or Firm*—George M. Gould; George W. Johnston; Mark E. Waddell

[57] ABSTRACT

Light screening compositions which contain a compound of the formula

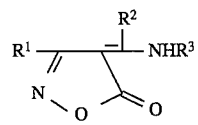

wherein $R^1$ represents H, $C_{1-19}$-alkyl, $C_{2-29}$-alkenyl, $C_{2-29}$-alkynyl, optionally lower-alkyl or oxy-lower alkyl substituted phenyl, $R^2$ represents H, $C_{1-29}$-alkyl, $C_{2-29}$-alkenyl, $C_{2-29}$-alkynyl, optionally lower-alkyl or oxy-lower alkyl substituted phenyl, $R^3$ represents H, $C_{1-19}$-alkyl, $C_{1-19}$-hydroxyalkyl, $C_{1-19}$-polyhydroxyalkyl, $C_{2-29}$-alkenyl, $C_{2-29}$-alkynyl, optionally lower-alkyl or oxy-lower alkyl substituted phenyl or optionally lower-alkyl or oxy-lower alkyl substituted pyridyl, a polyether residue, a phenylsulphonic acid residue and $R^2$ and $R^3$ together with the N atom can also form a ring.

4 Claims, No Drawings

LIGHT SCREENING AGENT

This is a divisional of U.S. application Ser. No. 08/361,869, filed Dec. 22, 1994, now U.S. Pat. No. 5,481,001, which is a continuation of U.S. application Ser. No. 07/949,853, filed Nov. 19, 1992, now abandoned.

The invention is concerned with light screening compositions which contain isoxazolones, namely compounds of the formula

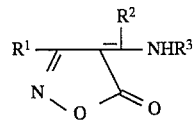   I wherein
- $R^1$ represents H, $C_{1-19}$-alkyl, $C_{2-29}$-alkenyl, $C_{2-29}$-alkynyl, optionally lower-alkyl or oxy-lower alkyl substituted phenyl,
- $R^2$ represents H, $C_{1-29}$-alkyl, $C_{2-29}$-alkenyl, $C_{2-29}$-alkynyl, optionally lower-alkyl or oxy-lower alkyl substituted phenyl,
- $R^3$ represents H, $C_{1-29}$-alkyl, $C_{1-19}$-hydroxyalkyl, $C_{1-19}$-polyhydroxyalkyl, $C_{2-29}$-alkenyl, $C_{2-29}$-alkynyl, optionally lower-alkyl or oxy-lower alkyl substituted phenyl or optionally lower-alkyl or oxy-lower alkyl substituted pyridyl, a polyether residue, a phenylsulphonic acid residue, and
- $R^2$ and $R^3$ together with the N atom can also form a ring.

The compounds of formula I are particularly suitable as light screening agents. The invention is accordingly also concerned with the use of I as light screening agents.

The compound of formula I are partly novel and partly known.

The novel compound I, namely the compounds I', correspond to those compounds of formula I above in which the sum of the carbon atoms of $R^1+R^2+R^3=9-30$ and the number of phenyl residues per molecule does not exceed 1, and the radical $R^1$ cannot be unsubstituted or substituted phenyl.

These novel compounds I and the process for their manufacture form further objects of the present invention.

The process comprises appropriately substituting an isoxazolone of the formula

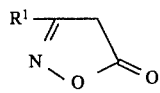   II wherein $R^1$ has the above significance, in the 4-position.

This substitution is conveniently effected with a $R^2$-substituted carboxylic acid derivative. There is thus formed a compound of the formula

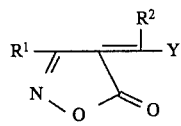   III

Y signifies $NHR^3$, OH, O-lower alkyl, halogen, $NH_2$, $NHR^5$.

Examples of the aforementioned carboxylic acid derivatives are

| | | |
|---|---|---|
| A | $R^2$—C(=$NR^3$)(—X) | wherein X = -halogen, —$OR^4$ (in which $R^4$ = lower alkyl) —$NHR^3$ |
| B | $R^2$—C(=$NR^5$)(—X) | $R^5$ = H, lower alkyl; ≠ $R^3$ |
| C | $R^2$—C(=$NH_2^+$)(—X) | |
| D | R—C(=O)(—X) | |
| E | $R^2$—C($OR^4$)$_3$ | |

They are thereby formed:

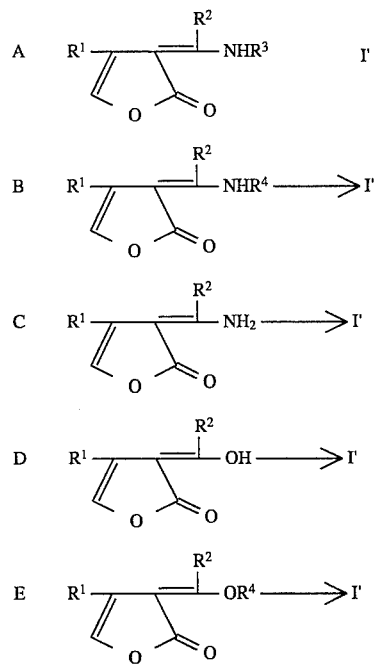

Where Y=$NHR^3$ in formula III the desired end product I' therefore results directly.

If, however, Y≠$NHR^3$ then the grouping Y=$NHR^3$ is conveniently introduced in a subsequent, secondary reaction step and the compound I' is thus obtained.

This is carried out e.g. by reacting the compound III with an amine $R^3NH_2$. In case C, $R^3$ can also be introduced by reaction with a halide $R^3Hal$ (F, Cl, Br, I) or a corresponding epoxide such as e.g. $(CH_2)_2O$, etc.

The secondary reaction step can be effected, e.g. in E, simultaneously with the primary reaction.

Depending on the structure of the amine $R^3NH_2$ or its residue $R^3$, which can carry more than one amino substituent, molecules with several. e.g. 2 or 3, isoxazole residues can also be formed.

One such amine would be e.g. a polyoxypropylenediamine, e.g. of the formula $NH_2CH[CH_3]CH_2(OCH_2CH_2[CH_3])_nNH_2$, or a polyoxy-ethylenediamine, e.g. of the formula $NH_2CH_2CH_2(OCH_2CH_2)_nNH_2$, in which n signifies e.g. a whole number of 1 to 30.

The reactions are conveniently carried out using methods per se.

A or the primary step of B–E is conveniently carried out in a temperature range of about 0°–150° C. It is carried out, if desired, in the presence of an inert solvent, e.g. diethyl ether, tetrahydrofuran, dioxan, toluene, xylene, dichloromethane, dichloroethane, etc.

If desired, the reaction is carried out in the presence of a base, preferably a weak base such as e.g. a tertiary amine, e.g. triethylamine, dimethylaniline, dimethylaminopyridine or diazabicyclooctane, or an inorganic base such as e.g. sodium phosphate, soda, potash, magnesium hydroxide or oxide; although sodium hydroxide or potassium hydroxide also comes into consideration. The reaction is conveniently carried out in a temperature range of 0°–200° C., especially of 20°–150° C.

In the case of the secondary step of B to E, the addition of the primary amine $R^3NH_2$ is conveniently effected in a temperature range of about 0°–200° C., especially of 50°–160° C., optionally under pressure. The use of a solvent is optional. The aforementioned solvents come into consideration.

In case of the halide $R^3Hal$, the addition of this halide is optionally effected in the presence of a base, preferably a strong base, e.g. an alcoholate, an amide, an alkali hydroxide, etc. The convenient temperature range is that given above. The addition of a solvent is optional.

In the case of the epoxide, its addition is conveniently effected in the presence of a catalyst, e.g. a strong base or a strong acid. Examples are: alkali hydroxides, alcoholates, mineral acids, Lewis acids, etc. The convenient reaction conditions are as given above.

The purification of the resulting compound I can be effected, for example, by crystallization or distillation.

The above reactions are in principle reactions with activated carboxylic acid derivatives, which are reacted with isoxazolones II which are unsubstituted in the 4-position.

The starting materials are known or can be prepared according to methods known per se. Thus, e.g., activated carboxylic acid derivatives are described in Houben-Weyl, Methoden der organischen Chemie [Volume E5 (1985)] by J. Falbe, and [Volume E4 (1983)] by H. Hagmann.

Suitable $C_{1-29}$-alkyl residues are, for example:

$C_{1-12}$-alkyl residues, but also higher, e.g. $C_{15}$-, $C_{18}$-, $C_{20}$-, $C_{21}$-, $C_{24}$-, $C_{27}$-, $C_{29}$- residues, and also lower alkyl $(C_{1-6})$ residues, e.g. methyl, ethyl, propyl, butyl, hexyl, etc.

Suitable $C_{2-29}$-alkenyl residues are, for example:

$C_{2-12}$-α-alkenyl, $C_{2-12}$-ω-alkenyl, $C_{2-6}$-alkenyl, especially allyl, methallyl, Δ2-butenyl, Δ3-butenyl, ω-hexenyl, etc.

Suitable $C_{2-29}$-alkynyl residues are in particular $C_{2-6}$-alkinyl residues, e.g. 2-propynyl, 3-butynyl, 4-pentynyl, 1,1-dimethylpropynyl, ω-hexinyl, etc.

Examples of lower-alkyl and, respectively, the lower-alkyl part of oxy-lower alkyl are: $OCH_3$, $OC_2H_5$, $OC_5H_{11}$, $OC_6H_{13}$, etc.

Examples of $C_{1-29}$-hydroxyalkyl residues are $CH_2CH_2OH$, $CH_2CH_2(CH_3)OH$, $CH(OH)(CH_2)_nH$ with n=2–28, or as illustrated e.g. in Example 16.

Examples of $C_{1-29}$-polyhydroxyalkyl residues are $CH_2CH(OH)CH_2OH$, $CH_2(CHOH)_nCH_2OH$, $(CHOH)_n$-$CH_2OH$, $CH(CHOH)_nCH_2OCHOH$, $CH(CHOH)_nCH(CH_2OH)OCHOH$ with n=1–28, especially 1–4.

Examples of polyether residues are polyethylene glycol residues, polypropylene glycol residues, e.g. $(CH_2CH_2O)_nH$ or $[CH(CH_3)CH_2O]_nH$ with n=2–20, as illustrated e.g. in Examples 18 and 19.

All the residues $R^1$, $R^2$ and $R^3$ can be straight-chain or branched.

$R^2$ and $R^3$ together with the N atom can also form a—saturated or unsaturated—ring, e.g. a 5- or 6-membered ring such as e.g. the pyrrolidinyl ring.

The total number of carbon atoms of $R^1$ and $R^2$ and $R^3$ conveniently does not exceed 30; because otherwise the relationship of the sizes of the residues $R^1$, $R^2$ and $R^3$ compared with the light-absorbing part of the molecule (chromophore, i.e. the isoxazolone part) is unfavourable.

The preferred residues in the case of the different substituents are as follows:

1) $R^1$=methyl, but also hexyl and phenyl, $R^2$=H or $C_{3-11}$-alkyl, $R^3$=$C_{3-20}$-alkyl, substituted phenyl;
2) as 1) whereby $R^2$ and $R^3$ together have 5–15, especially 9–13, C atoms;
3) as 1), whereby $R^2$=H and $R^3$=$C_{8-16}$-alkyl, especially $C_{10-12}$-alkyl;
4) $R^1$=methyl, but also hexyl and phenyl, $R^2$ or $R^3$=phenyl, pyridyl, optionally substituted, and the other residue ($R^3$ or $R^2$)=$C_{5-20}$-alkyl, especially $C_{7-14}$- or $C_{9-12}$-alkyl.

Essential requirements of (especially cosmetic) UV filters are e.g.:

high extinction (1) (and associated therewith low dosing and therefore reduced toxicological risk);

high stability against the influence of light (2);

stability against acids, bases, air and other chemical or thermal influences (3);

good oil solubility (4) and/or good water solubility;

low tendency to crystallize-out, e.g. from emulsions even at low temperatures (e.g. in snow);

toxicological safety;

lack of colour and lack of smell (5);

favourable price, inexpensive to use (6);

water resistance (substantivity);

very good compatibility with other cosmetic ingredients and simplicity in handling (7).

The compounds I' are very well suited as light screening agents because they generally fulfil a majority of the foregoing requirements, especially parameters (1), (2), (3), (4), (5), (6) and (7) set forth above.

It is quite generally true that the UV filters of structure I are novel chromophores having a high photostability.

The compounds of Examples 1, 2, 3, 4, 10, 11, 12, 14, 15, 16, 18, 20 and 21 hereinafter are especially preferred because they fulfil these requirements in a particular manner.

The manufacture of the novel light screening compositions (especially of skin protection and, respectively, sunscreen preparations for everyday cosmetics) comprises incorporating a compound of general formula I into a cosmetic base which is suitable for light screening compositions. Where convenient, other conventional UV A or UV B filters can also be combined during this incorporation.

Such UV A filters are, for example:

1-(4-methoxyphenyl)-3-(4-tert.-butylphenyl)propane-1,3-dione CTFA name: butylmethoxydibenzoylmethane 4-Isopropyl-dibenzoylmethane 2,2'-Hydroxy-4-methoxybenzophenone (=dioxybenzone or benzophenone-δ)

2-Hydroxy-4-methoxybenzophenone-5-sulphonic acid (=sulisobenzone, benzophenone-4)

2-Hydroxy-4-methoxybenzophenone (=oxybenzone, benzophenone-3)

3,3,5-Trimethyl-cyclohexyl-N-acetyl-anthranilate (=homomenthyl N-acetyl-anthranilate)

2-Methylanthranilate

Usual UV B filters such as, for example, the following organic compounds belonging to the widest classes of substances can be mentioned as UV B filters i.e. as substances having absorption maxima between about 290 and 320 nm:

1) p-Aminobenzoic acid derivatives, such as e.g. ethyl p-aminobenzoate and other esters, such as propyl, butyl, isobutyl p-aminobenzoate, ethyl p-dimethylaminobenzoate, glyceryl p-aminobenzoate, amyl p-dimethylaminobenzoate.
2) Cinnamic acid derivatives such as e.g. 2-ethoxyethyl p-methoxycinnamate, 2-ethylhexyl p-methoxycinnamate, p-methoxycinnamic acid ester mixtures, cinnamic acid ester mixtures.
3) Dibenzalazine.
4) Heterocyclic nitrogen compounds such as 2-phenylbenzimidazole derivatives, e.g. 2-phenylbenzimidazole-5-sulphonic acid.
5) Salicylic acid derivatives such as e.g. menthyl salicylate, homomenthyl salicylate, phenyl salicylate.
6) Benzophenone derivatives such as e.g. 4-phenylbenzophenone, 4-phenylbenzophenone-2-carboxylic acid isooctyl ester, 2-hydroxy-4-methoxybenzophenone-5-sulphonic acid.
7) Coumarin derivatives such as e.g. 7-oxycoumarin, β-umbelliferoneacetic acid, 6,7-dioxycoumarin.
8) Gallic acid derivatives such as e.g. digalloyl trioleate.
9) Arylidenecycloalkanones such as e.g. benzylidenecamphor.
10) Anthranilic acid derivatives such as e.g. menthyl anthranilate.
11) Hydroxyphenylbentriazole.

As usual cosmetic bases for the light screening compositions in the scope of the present invention there can be used any usual preparation which corresponds to the cosmetic requirements, e.g. creams, lotions, emulsions, salves, gels, solutions, sprays, sticks, milks and the like. The light screening effect will, of course, also be dependent on the base which is used. The intensity of the light screening activity also depends in the case of the same base on the concentration of active ingredient. Suitable concentrations are e.g. between 1–6%, preferably between 2–5%, of a compound of formula I in the cosmetic preparation.

The light screening agents are, however, also suitable against the damaging influence of light on other substrates to be protected. As such further substrates there come into consideration e.g.: plastics and synthetic resins, soft resins, e.g. for contact lenses, varnishes, oils, waxes, furniture and car polishes, etc.

Example 1

4-[1-(N-Pentylamino)-1-hexylidene]-3-methylisoxazol-5(4H)-one a) N-Pentyl-caproamide 275 g of caproyl chloride are added dropwise within 30 minutes to a solution of 500 ml of n-pentylamine in 1.4 l of methylene chloride while cooling with ice and stirring. After standing at room temperature for 4 hours the reaction solution is washed in succession with 1 l of 0.1N HCl, 1 l of 0.1N NaOH and 1.5 l of NaCl solution. The organic phase is concentrated on a rotary evaporator and dried in a high vacuum and gives 370 g of a crystalline mass (98% of theory). M.p. 37° C.

b) N-Pentyl-hexaneiminoyl chloride 81 g of the amide prepared above are dissolved in 800 ml of $CCl_4$ and treated portionwise with 91 g of phosphorus pentachloride. This mixture is held at reflux temperature for 3 hours, whereby HCl evolves. Now, $CCl_4$ and $POCl_3$ are distilled off and finally the product is fractionated in a high vacuum at 80°–85° C./0.2 mbar. Yield 62 g of a colourless oil (70% of theory). NMR ($CDCl_3$): 3.44 (t/2H); 2.62 (t/2H); 1.8–1.55 (multiplet/4H); 1.5–1.2 (multiplet/8H); 1.0–0.82 (multiplet/6H).

c) 4-[1-(N-Pentylamino])-1-hexylidene]-3-methylisoxazol- 5(4H)-one 8 g 3-methylisoxazol-5(4H)-on [prepared according to A. R. Katritzky et al., Tetrahedron 18, 777 (1962)] and 17.9 g of triethylamine are stirred in 320ml of dioxan for 15 minutes and now treated with 16.5 g of the N-pentyl-hexaneiminoyl chloride prepared above. The reaction mixture is held at reflux temperature for 150 minutes and, after cooling, poured into 800 ml of 2N HCl. Now, the mixture is extracted three times with ether and back-washed with NaCl solution. The organic phases, dried over $Na_2SO_4$, are concentrated and dried in a high vacuum and give 20 g (93%) of a brown mass which is recrystallized in hexane. M.p. 36° C. IR (KBr): 1670; 1620; 1547. NMR ($CDCl_3$): 10.4 ppm (s,broad/NH); 3.42 (Q/2H); 2.62 (symmetr. multiplet/2H); 2.30 (s/3H); 1.8–1.3 (multiplet/12H); 0.94 (symmetr. multiplet/6H). MS: 266(100%), 223, 209, 112. UV (EtOH): 311 nm (ε=17900).

Example 2

4-[1'-(N-Pentylamino)-1-hexylidene]-3-phenylisoxazol-5(4H)-one

The procedure described in Example 1 is repeated, but 3 -phenylisoxazol-5(4H)-one [prepared according to A. Hanzsch, Berichte 24, 502 (1891)] is used in section c) in place of 3 -methylisoxazol-5(14H)-one. The named product is obtained in 74% yield as a crystalline powder (m.p. 71° C.). (UV EtOH): 314 nm (ε=18000).

Example 3

4-[1'-(N-Pentylamino)-1-hexylidene]-3-n-hexylisoxazol-5(4H)one

The procedure described in Example 1 is repeated, but 3 -n-hexylisoxazol-5(4H)-one is used in section c) in place of 3 -methylisoxazol-5(4H)-one. The named product is obtained in 51% yield as a yellowish oil. UV (EtOH): 313 nm (ε=17593).

3-n-Hexylisoxazol-5(4H)-one is obtained in 99% yield as a reddish liquid by holding ethyl 3-oxo-pelargonate at reflux temperature for 1 hour with one equivalent of hydroxylamine hydrochloride and one equivalent of pyridine and thereafter working-up in the usual manner.

Example 4

4-[1'-(N-Phenylamino)-1-heptylidene]-3-methylisoxazol-5(4H)-one

The procedure described in Example 1 is repeated, but in section a) aniline is used in place of n-pentylamine and n-heptanoyl chloride is used in place of caproyl chloride. N-Phenyl-n-heptenamide (m.p. 50° C.) is obtained in 94% yield. This is reacted with $PCl_5$ as in Example 1, section b), and gives in quantitative yield N-phenyl-heptaneiminoyl chloride as a yellowish oil which is converted according to section c) into the desired product and purified by chromatography on silica gel in hexane/ether=1:1. M.p. 83°–84° C. UV (EtOH): 320 nm (ε=19502).

Example 5

4-(2'-Pyrrolidenyl)-3-methylisoxazol-5(4H)-one 2 g of 3-methylisoxazol-5(4H)-one [prepared according to A. Katritzky et al., Tetrahedron 18, 777 (1962)] are treated with 2 g of 2-methoxy-Δ1-pyrroline [prepared according to A. E. Wick et al., Helv. 54, 513 (1971)] and left to stand for 2 days. The resulting crystal mass is recrystallized in ethanol and gives white crystals of the desired product in 60% yield. M.p. 188°–190° C. UV: 302 nm ($\epsilon$=18100).

Example 6

4-[1'-(N-Isopropylamino)-1-hexylidene]-3-methylisoxazol-5(4H)-one

N-isopropyl-caproamide is prepared in the same manner as in Example 1, section a), from caproyl chloride and isopropylamine (yield 80%, b.p. 87° C./0.1 Torr). 11 g thereof are added dropwise to 7 ml of dimethyl sulphate and the mixture is stirred at 25° C. for 24 hours. By partition between aqueous potash solution and ether and subsequent concentration and distillation of the organic phase there are obtained 6.7 g (56%) of a yellowish liquid of N-isopropylcaproamide iminomethyl ether (b.p. 50° C./16 Torr). When this iminoether is now held at reflux temperature in an analogous manner to that in Example 1, section c), with one equivalent of 3-methylisoxazol-5(4H)-one and 0.03 equivalent of 1,4-diazabicyclo[2.2.2]octane for 40 hours in toluene, then, after working-up and recrystallization from hexane/ether=1:1, the desired product is obtained in 20% yield. M.p. 99°–101° C., UV (EtOH): 310 nm ($\epsilon$=17350).

Example 7

4-(1'-Amino-1'-dodecylidene)-3-methylisoxazol-5(4H)-one

Gaseous hydrochloric acid is conducted into a solution of 90 g of lauronitrile and 23 g of ethanol while cooling with ice for 60 minutes. A crystalline mass forms after standing for 48 hours and this is freed from excess HCl and ethanol on a rotary evaporator. The procedure described in Example 1, section c), is repeated with the crude lauramide iminoethyl ether hydrochloride obtained, i.e. it is added dropwise to a solution of 3-methylisoxazol-5(4H)-one and triethylamine in dioxan and stirred at 25° C. for 24 hours. After the usual working-up the desired product is obtained in 98% yield as orange crystals and is recrystallized from hexane/ethyl acetate=1:1. M.p. 105°–106° C., UV: 302 nm ($\epsilon$=15000).

Example 8

4-(1'-Amino-1'-pentylidene)-3-methylisoxazol-5(4H)-one

When the procedure described in Example 7 is repeated using valeronitrile in place of lauronitrile, then the above product is obtained as a white crystalline powder. M.p. 113°–115° C., UV: 302 nm ($\epsilon$=16270).

Example 9

4-(1'-Ethylamino-1'-dodecylidene)-3-methylisoxazol-5(4H)-one 3.6 g of lauronitrile are held at reflux temperature for 24 hours with 7.6 g of triethyloxonium fluoroborate in 20 ml of methylene chloride. Now, the reaction mixture is added dropwise to a solution of 2 g of 3-methylisoxazol-5(4H)-one and 6 g of triethylamine in 60 ml of toluene and the mixture is held at reflux temperature overnight. By partitioning between 2N hydrochloric acid and ether and concentration of the organic phase there is obtained a brown oil which, by purification using chromatography with $CH_2Cl_2$/methanol= 100:1, gives the desired product as yellow crystals in 60% yield. M.p. 67° C., UV (EtOH): 312 nm ($\epsilon$=20405).

4(Z)-[1'-(2"-Ethylhexyl)-amino-1'-heptylidene]-3-methyl-isoxazol-5(4H)-one, (m.p. 0°–5° C.), is obtained in an analogous manner when there is used as the starting material in place of 4-(1'-amino-1'-dodecylidene)-3-methylisoxazol-5(4H)-one in accordance with Example 7 4-(1'-amino-1'-heptylidene)-3-methylisoxazol-5(4H)-one (m.p. 91° C., prepared with n-heptanonitrile in place of lauronitrile).

Likewise, 4(Z)-(1'-hexylamino-2'-methyl-1'-butylidene)-3-methylisoxazol-5(4H)-one is obtained in an analogous manner as a colourless liquid when there is used as the starting material in place of 4-(1'-amino-1'-dodecylidene)-3-methylisoxazol-5(4H)-one in accordance with Example 7 4-(1'-amino-2'-methyl-1'-butylidene)-3-methylisoxazol-5(4H)-one (m.p. 132° C., prepared with 2-methyl-butyronitrile in place of lauronitrile). [In this latter case, n-hexylamine is used in place of 2-ethyl-1-hexylamine].

Example 10

4-[1'-N-(2"-Ethylhexyl)-1'-dodecylidene]-3-methylisoxazol-5(4H)-one 2.8 g of 4-(1'-amino-1'-dodecylidine)-3-methylisoxazol-5(4H)-one, prepared in Example 7, are heated at 100° C. for 4 hours with 2 g of 2-ethyl-1-hexylamine, whereby ammonia is liberated. The reaction mixture is partitioned between aqueous $NaH_2PO_4$ solution and ether and the ether phases are concentrated and filtered over silica gel in hexane/ether= 1:1. 2.9 g (74% yield) of the desired product are obtained as a yellow oil. MS: 392, 293(100%), 265, 154. UV (ethanol): 313 nm ($\epsilon$=18600).

Example 11

4-(1'-N-2-Dodecylaminobenzylidene)-3-methylisoxazol-5(4H)-one 1 g of 4-benzoyl-5-hydroxy-3-methylisoxazole [prepared according to K. Sato et al., Chem. Pharm. Bull 34, 3153 (1986)] is heated at 150° C. for 15 minutes with 1 g of n-dodecylamine and thereupon the reaction mixture is partitioned between aqueous $NaH_2PO_4$ solution and ether. After evaporation of the ether phases the desired product is obtained as a yellow cyrstalline powder. M.p. 52° C. MS: 370, 369, 341, 215(100%), 185. UV (EtOH): 317 nm ($\epsilon$=17235).

Example 12

4-(N-n-Dodecylaminomethylidene)-3-methylisoxazol-5(4H)-one 3 g of triethyl orthoformate are added to 3.7 g of n-dodecylamine and 2 g of 3-methylisoxazol-5(4H)-one and the reaction mixture is heated at 60° C. for 20 hours. Thereupon, it is filtered over silica gel in hexane/ether/$CH_2Cl_2$=1:1:3 and the desired product obtained is recrystallized in hexane. Yield 29%, m.p. 57° C., UV (EtOH): 311 nm ($\epsilon$=18530).

Example 13

4-(p-Isopropylanilino-1'-ethylidene)-3-methylisoxazol-5(4H)-one 3.25 g of triethyl orthoacetate are added to 2.7 g of p-isopropylaniline and 2 g of 3-methylisoxazol-5(4H)-one and the reaction mixture is heated at 80° C. for 24 hours. The cooled, crystallized-out reaction mixture is recrystallized in ethanol/ether/hexane/ethyl acetate=1:1:1:1, whereby the desired product is obtained in 65% yield as yellow crystals. M.p. 170° C., UV (EtOH): 324 nm ($\epsilon$=21800).

Example 14

4(Z)-(p-n-Hexylanilinomethylidene)-3-hexylisoxazol-5(4H)-one 1.7 g of 3-n-hexylisoxazol-5(4H)-one (prepared in accordance with Example 3) are dissolved in 10 ml of triethyl orthoformate and heated at 80° C. for 2 hours together with 2.65 g of p-hexylaniline. The dark reaction solution is concentrated and recrystallized in 100 ml of hexane. 1.8 g (50% of theory) of the above-named crystalline compound are obtained. M.p. 88°–90° C., UV (EtOH): 356 nm ($\epsilon$=26469). This compound is especially suitable as a UV A filter.

Example 15

4-[1'-(N-Butylamino)-1'-hexylidene]-3-methylisoxazol-5(4H)-one a)
4-(1'-Oxy-1'-hexylidene)-3-methylisoxazol-5(4H)-one 9.9 g of 3-methylisoxazol-5(4H)-one [prepared according to A. R. Katritzky et al., Tetrahedron 18, 777 (1962)] in 200 ml of dichloromethane are treated with 48 g of 4-N,N-dimethylaminopyridine and subsequently with 16.9 g of caproyl chloride and the mixture is held at reflux temperature for 5 hours. The red coloured reaction solution obtained is partitioned between 1N hydrochloric acid and ethyl acetate and the ethyl acetate phases are back-extracted, dried over $Na_2SO_4$ and concentrated on a rotary evaporator. A crude oil is obtained in quantitative yield: NMR ($CDCl_3$): 0.92 (t/3H); 1.38 (multiplet/4H); 1.75 (multiplet/2H); 2.36 (s/3H); 2.67 (dxd/2H); 8.9 (s,broad/1H); UV (EtOH): 280 nm ($\epsilon$=13714).

b)
4-(1'-[N-Butylamino]-1'-hexylidene)-3-methylisoxazol-5(4H)-one 4.9 g of the crude product obtained above are treated with 3.7 g of n-butylamine while cooling and heated at 150° C. in an autoclave for 30 minutes. After cooling, the cooled crude product is recrystallized three times from a mixture of methyl tert.butyl ether and hexane, there being obtained 2.8 g (45%) of beige coloured crystals. M.p. 62°–63° C. UV (EtOH): 312 nm ($\epsilon$=17980).

Example 16

4(Z)-Ethanolamino-methylidene-3-methylisoxazol-5(4H)-one 49.5 g of 3-methylisoxazol-5(4H)-one are dissolved in 125 ml of orthoformic acid and treated slowly at 0° C. with 30.5 g of 2-aminoethanol. After stirring for 60 minutes the mixture is cooled to 5° C. and the resulting crystals are filtered off under suction and washed with ether. There are thus obtained 60 g of the desired water-soluble product which is recrystallized in methanol. M.p. 135° C., UV (EtOH): 310 nm ($\epsilon$=17,800). Having regard to the good water solubility, this UV-filter is especially suitable for use in the aqueous phase of sunscreen emulsions.

Example 17

Bis-[3-methylisoxazol-5(4H)-ono-4-(1'-ethylidene-1'-amino-2"-propyl-1"-oxy)]-polypropylene glycol ether a)
4-(1'-Ethoxy-1'-ethylidene)-3-methylisoxazol-5(4H)-one 19.8 g of 3-methylisoxazol-5(4H)-one are dissolved in 50 ml of triethyl orthoacetate and, after 10 minutes, the resulting crystallizate is filtered off under suction and rinsed with hexane. There are obtained 32.6 g of pale coloured crystals of the desired intermediate. M.p. 126°–127° C.; UV (EtOH): 294 nm ($\epsilon$=12,000).

b) Bis-[3-methylisoxazol-5(4H)-ono-4-(1'-ethylidene-1'-amino-2"-propyl-1"-oxy)]-polypropylene glycol ether 8.45 g of the heterocyclic enol ether obtained above are held at reflux temperature for 200 minutes together with 12 g (0.6 equivalents) of polyoxypropylenediamine (BASF; Ludwigshafen, Aetheramin 400; CAS Reg. No. 9046-10-0) in 50 ml of toluene. The reaction mixture is shaken several times between methylene chloride and 1N aqueous sulphuric acid and the organic phases are concentrated. The desired product is obtained as a clear yellowish resin in almost quantitative yield. UV (EtOH): 309 nm (E=505): NMR ($CDCl_3$): 1.1 m/18H($CH_3$); 1.3 m/6H($CH_3$); 2.3 s/6H($CH_3$); 2.4 s/6H($CH_3$); 3.3–4.1 m, broad/24H; 10.4 s/2H(NH).

Example 18

4(Z)-[1'-(2"-Hydroxyethoxy-2"-ethylamino)-1'-pentylidene]-3-methylisoxazol-5(4H)-one 1.8 g of the 4-(1'-amino-1'-pentylidene)-3-methyl-isoxazol-5(4H)-one are heated to reflux temperature in 200 ml of ethanol and treated with 1.58 g of 2-(2'-aminoethoxy)ethanol. After 30 minutes the reaction mixture is cooled and the separated crystals are filtered off under suction and recrystallized in 50 ml of ethanol. There are obtained 1.1 g of white crystals of the desired product. M.p. 100° C.; UV (EtOH): 312 nm ($\epsilon$=17709).

Example 19

4(Z)-(1'-Ethanol-amino)-1'-heptylidene]-3-methylisoxazol-5(4H)-one 9.1 g of the 4-(1'-amino-1'-pentylidene)-3-methylisoxazol- 5(4H)-one are heated to 100° C. in an autoclave for 2 hours together with 8 equivalents (17.6 g) of ethylene oxide and 40 mg of sodium methylate. The crude product obtained is partitioned between methylene chloride and water, the methylene chloride phase is concentrated and chromatographed over silica gel. There is obtained the desired product as the main component in addition to 4(Z)-[1'-(1"-desoxy-polyethyleneglycol-1"-amino)-1'-heptylidene-3-methyl-isoxazol-5( 4H)-one.

Example 20

4(Z)-[p-Potassiumsulphonato-anilinomethylidene]-3-methyl-isoxazol-5(4H)-one 9.9 g of 3-methylisoxazol-5(4H)-one are stirred in 25 ml of triethyl orthoformate for 10 minutes and subsequently treated with 17.3 g of p-sulphanilic acid. After heating to reflux temperature for 15 minutes the mixture is cooled and the resulting crystalline mass is washed with ether and thereupon treated with one equivalent of aqueous KOH and concentrated. There are obtained 16.5 g of yellow crystals of the desired product which still contains sulphanilic acid salt. The pure product is obtained by recrystallization in ethanol. M.p.>240° C. This is a water-soluble UV-A filter. UV (EtOH): 349 nm ($\epsilon$=21513).

Example 21

4(Z)-[1'-(2"-Ethyl)-hexylaminomethylidene]-3-methylisoxazol-5(4H)-one 49.5 g of 3-methylisoxazol-5(4H)-one are heated to 75° C. in 125 ml of trimethyl orthoformate and treated simultaneously with 64.5 g of 2-ethyl-1-hexylamine and with 23 g of formic acid. After heating to reflux temperature for 2 hours the reaction mixture is partitioned between ice-water and methyl t-butyl ether (MTBE) and the organic phase is concentrated. There are obtained 95.7 g of a red, viscous oil which is recrystallized from MTBE/hexane. M.p. 40° C.; UV (EtOH): 312 nm ($\epsilon$=19040).

Example 22

4(Z)-[1'-N-(2"-Aminopyridino)-1'-ethylidene]3-methylisoxazol-5(4H)-one 3.3 g of the 4-(1'-ethoxy-1'-ethylidene)-3 -methylisoxazol-5(4H)-one prepared in Example 17a) and 1.9 g of 2-aminopyridine are heated to 60° C. Now, the oil bath heating is adjusted to 100° C. for 30 minutes. The cooled product is now recrystallized in methylene chloride and diethyl ether. Yield 2.4 g of desired product. M.p. 132° C.; UV (EtOH): 342 nm ($\epsilon$=23516). It is a UV-A filter.

All compounds of the above Examples are novel compounds I. Preferred derivatives are those of Examples 1, 2, 3, 4, 10, 11, 12, 14, 15, 16, 18, 20, 21.

Example 23

| A. Oil/water sunscreen lotion | % wt./wt. |
|---|---|
| A) Compound of Example 1 | 6.00 |
| Glyceryl myristate | 4.00 |
| Cetyl alcohol | 0.50 |
| Dimethicone[2] | 0.50 |
| Coco caprylate/caproate[3] | 5.00 |
| Methyl/propylparaben[4] | 0.25 |
| Propylene glycol | 2.50 |
| Castor oil (hydr.) | 2.00 |
| B) Potassium cetyl phosphate | 2.00 |
| C) Water | 74.65 |
| Propylene glycol | 2.50 |
| Na$_2$ EDTA | 0.10 |
| | 100.00 |

[2] (linear dimethylsiloxane polymer)
[3] Mixture of esters of coconut alcohol with caprylic acid and caproic acid
[4] Mixture of methyl p-hydroxybenzoate and propyl p-hydroxybenzoate

| B. Oil/water sunscreen cream | % wt./wt. |
|---|---|
| A) Compound of Example 1 | 6.00 |
| Glyceryl stearate | 10.00 |
| PEG-1000 stearate[1] | 3.00 |
| Isopropyl myristate | 3.00 |
| PEG-7 glyceryl cocoate[2] | 6.00 |
| Methyl/propylparaben | 0.25 |
| B) Water | 66.65 |
| Na$_2$ EDTA | 0.10 |
| Propylene glycol | 5.00 |
| C) Odorant | q.s. |
| | 100.00 |

[1] Polyoxyethylene(1000)glycol monostearic acid ester
[2] Fatty acid glycerol monoester polyethylene(7)glycol ether

| C Oil/water sunscreen cream | % wt. % wt |
|---|---|
| A) Cetyl alcohol | 1.00 |
| Glyceryl stearate | 4.00 |
| Dimethicone | 0.30 |
| Coco caprylate/caproate | 8.00 |
| Compound of Example 15 | 3.00 |
| B) Amphisol K | 2.00 |
| C) Water | q.s. to 100 |
| Carbomer 951[1] | 0.10 |
| Na$_2$ EDTA | 0.10 |
| Methylparaben | 0.15 |
| D) KOH 10% | 0.60 |
| E) Phenoxyethanol & methylparaben & ethylparaben & propylparaben | 0.35 |
| F) Odorant | q.s. |

[1] Synthetic polymer from acrylic acid, cross-linked with an allyl ether of pentaerythritol.

I claim:

1. A light screening composition which comprises an effective ultraviolet absorbing amount of a compound of the formula

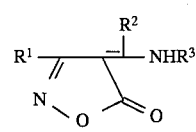

wherein $R^1$ represents H, $C_{1-19}$-alkyl, $C_{2-29}$-alkenyl, $C_{2-19}$-alkynyl, phenyl, lower-alkyl substituted phenyl or oxy-lower alkyl substituted phenyl, $R^2$ represents H, $C_{1-29}$-alkyl, $C_{2-29}$-alkenyl, $C_{2-29}$-alkynyl, phenyl, lower-alkyl substituted phenyl or oxy-lower alkyl substituted phenyl, $R^3$ represents H, $C_{1-19}$-alkyl, $C_{1-19}$-hydroxyalkyl, $C_{1-19}$-polyhydroxyalkyl, $C_{2-29}$-alkenyl, $C_{2-29}$-alkynyl, phenyl, lower-alkyl substituted phenyl, oxy-lower alkyl substituted phenyl, pyridyl, lower alkyl substituted pyridyl, oxy-lower alkyl substituted pyridyl, a polyether residue, a phenylsulphonic acid residue and $R^2$ and $R^3$ together with the N atom can also form a ring, and at least one substrate subject to degradation by light.

2. A light screening composition in accordance to claim 1 wherein $R^3$ represents H, $C_{1-19}$-alkyl, $C_{2-29}$-alkenyl, $C_{2-29}$-alkynyl, phenyl, lower-alkyl substituted phenyl, oxy-lower alkyl substituted phenyl, pyridyl, lower-alkyl substituted pyridyl or oxy-lower alkyl substituted pyridyl.

3. A light screening composition in accordance to claim 2 which contains a compound selected from the group consisting of 4-(1-(N-pentylamino)-1-hexylidene)-3-methylisoxazol-5(4H)-one, 4-(1'-(N-pentylamino)-1-hexylidene)-3-phenylisoxazol-5(4H)-one, 4-(1'-(N-pentylamino)-1-hexylidene)-3-n-hexylisoxazol-5(4H)-one, 4-(1'-(N-phenylamino)-1-heptylidene)-3-methylisoxazol-5(4H)-one, 4-(1'-N-(2"-ethylhexyl)-1'-dodecylidene)-3-methyl-isoxazol-5(4H)-one, 4-(1'-N-(2-dodecylaminobenzylidene)-3-methylisoxazol-5(4H)-one, 4-(N-n-dodecylaminomethylidene)-3-methylisoxazol-5((4H)-one, 4-(p-n-hexylanilinomethylidene)-3-hexylisoxazol-5(4H)-one, and 4-(1'-(N-butylamino)-1'-hexylidene)-3-methylisoxazol-5(4H)-one.

4. A light screening composition in accordance to claim 1 which contains a compound selected from the group consisting of 4-(ethanolamino-methylidene)-3-methylisoxazol-5(4H)-one, 4-(1'-(2"-hydroxyethoxy-2"-ethylamino)-1'-pentylidene)-3-methylisoxazol- 5(4H)-one, 4-(p-potassium sulphonato-anilinomethylidene)-3-methyl-isoxazol-5(4H)-one and 4-(1'-(2"-ethyl)-hexylaminomethylidene)-3-methyl-isoxazol-5(4H)-one.

\* \* \* \* \*

UNITED STATES PATENT AND TRADEMARK OFFICE
CERTIFICATE OF CORRECTION

PATENT NO. : 5,536,453
DATED : July 16, 1996
INVENTOR(S) : Ulrich Huber

It is certified that error appears in the above-indentified patent and that said Letters Patent is hereby corrected as shown below:

ON THE TITLE PAGE:

delete "[22] Filed Sep. 25, 1995" and insert --[22] PCT Filed: Mar. 23, 1992--.

Item [62], after abandoned, insert --, filed as PCT/EP92/00635, Mar. 23, 1992--.

Signed and Sealed this

Fifth Day of August, 1997

*Attest:*

BRUCE LEHMAN

*Attesting Officer*  *Commissioner of Patents and Trademarks*